United States Patent [19]

Mullaart et al.

[11] Patent Number: 5,562,813
[45] Date of Patent: Oct. 8, 1996

[54] TWO-DIMENSIONAL ELECTROPHORESIS APPARATUS AND AN ELECTROPHORESIS UNIT THEREFOR

[75] Inventors: Erik Mullaart, Nootdorp; André G. Uitterlinden, Rotterdam; Jan Vijg, Zegveld, all of Netherlands

[73] Assignee: Ingeny B.V., Leiden, Netherlands

[21] Appl. No.: 436,199

[22] PCT Filed: Sep. 24, 1993

[86] PCT No.: PCT/NL93/00191

§ 371 Date: Jun. 26, 1995

§ 102(e) Date: Jun. 26, 1995

[87] PCT Pub. No.: WO94/11730

PCT Pub. Date: May 26, 1994

[30] Foreign Application Priority Data

Nov. 17, 1992 [NL] Netherlands ............................ 92.02000

[51] Int. Cl.[6] .................................................. G01N 27/26
[52] U.S. Cl. ........................... 204/618; 204/467; 204/616; 204/466
[58] Field of Search ............................ 204/299 R, 180.1, 204/182.8, 182.1, 467; 7/618

[56] References Cited

U.S. PATENT DOCUMENTS

| | | | |
|---|---|---|---|
| 4,088,561 | 5/1978 | Anderson | 204/299 R |
| 4,148,703 | 4/1979 | Trop et al. | 204/180 G |
| 4,693,804 | 9/1987 | Serwer | 204/182.1 |
| 4,915,811 | 4/1990 | Yamamoto et al. | 204/299 R |
| 5,080,769 | 1/1992 | Fassett et al. | 204/180.1 |
| 5,108,567 | 4/1992 | Kölble | 204/180.1 |

*Primary Examiner*—Kathryn Gorgos
*Assistant Examiner*—Alex Noguerda
*Attorney, Agent, or Firm*—Webb Ziesenheim Bruening Logsdon Orkin & Hanson, P.C.

[57] ABSTRACT

The invention relates to an apparatus for two-dimensional electrophoresis of at least one electrophoresis unit comprising an electrophoresis medium enclosed between two plates, which apparatus comprises a first pair and a second pair of compartments for electrophoresis liquid which are provided with electrodes and which make electrophoretic contact on either side and mutually transversely of each other with the electrophoresis medium of the electrophoresis unit, wherein the compartments are disposed and adapted such that the electrophoresis unit assumes a standing position in the apparatus, and to an electrophoresis unit intended for such an apparatus.

20 Claims, 7 Drawing Sheets

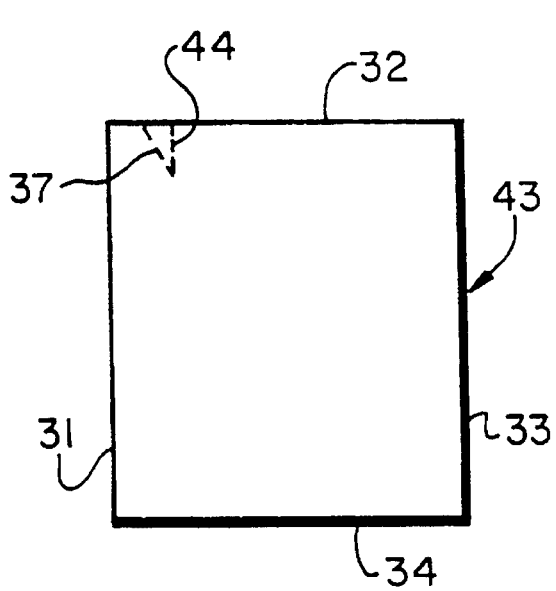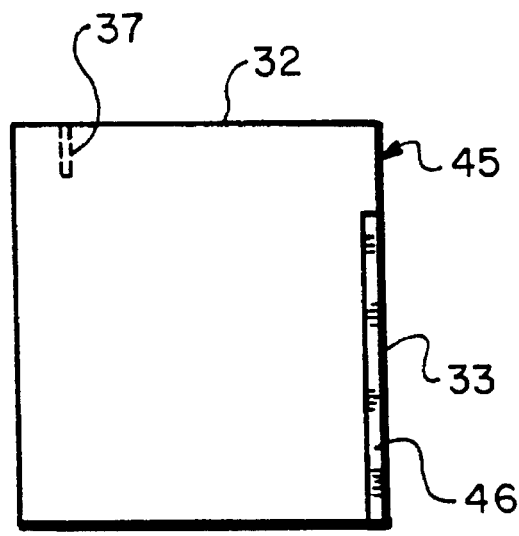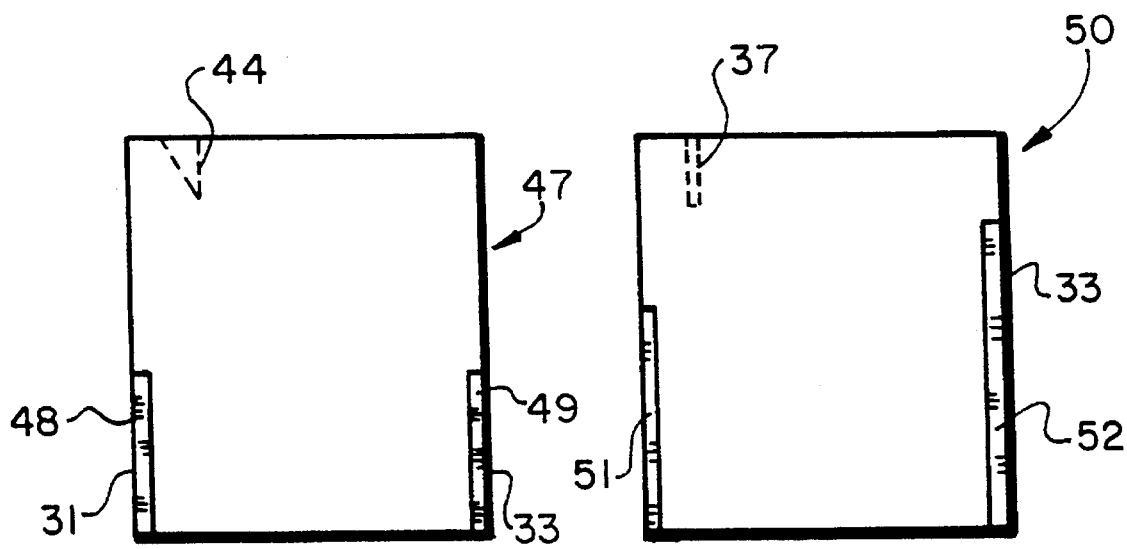

TWO-DIMENSIONAL ELECTROPHORESIS APPARATUS AND AN ELECTROPHORESIS UNIT THEREFOR

BACKGROUND OF THE INVENTION

1. Field of the Invention

The present invention relates to a two-dimensional electrophoresis apparatus, more particularly to a two-dimensional electrophoresis apparatus wherein an electrophoresis unit comprising an electrophoresis medium enclosed between two plates is disposed vertically in the electrophoresis apparatus.

2. Description of the Prior Art

The apparatus according to the invention has been developed particularly for two-dimensional electrophoresis in the case of DNA characterization (U.S. Pat. No. 5.068.167) but can also be used for two-dimensional electrophoresis of proteins (O'Farrell, PH et al., Journal Biological Chemistry, 250, pp 4007–4021 (1975)). In principle the two-dimensional electrophoresis apparatus according to the invention is suitable for electrophoresis of all kinds of charged materials.

At the moment two-dimensional electrophoresis is for instance applied in genetic studies in which frequently large numbers of samples of individuals must be subjected to electrophoresis under identical conditions. The known two-dimensional electrophoresis of DNA comprises electrophoresis in the first dimension in a gel, whereafter the different gel strips are cut out and placed on a gel for electrophoresis in the second dimension. This procedure is labour-intensive and requires highly trained personnel. Moreover, as a result of the various treatments, artefacts occur (for instance due to stretching or breaking of the gel) which results in a decrease in the reproducibility of the obtained separation patterns.

The present invention has for its object to provide a two-dimensional electrophoresis apparatus which substantially does not have the above stated drawbacks and with which large numbers or electrophoreses of different samples can moreover be performed simultaneously under substantially identical conditions, while handling or preparing of the electrophoresis medium between the first and second dimension electrophoresis is substantially wholly avoided. A substantially horizontal disposition of the electrophoresis unit in the electrophoresis apparatus is furthermore dispensed with since a vertically disposed electrophoresis unit can be sampled more conveniently. It is nevertheless possible according to the invention to leave the construction of the apparatus as simple as possible.

SUMMARY OF THE INVENTION

The above object is achieved according to the invention with an apparatus for two-dimensional electrophoresis provided with an electrophoresis unit comprising an electrophoresis medium enclosed between two plates in that a first pair and a second pair of compartments for electrophoresis liquid which are provided with electrodes make electrophoretic contact on either side and mutually transversely of each other with the eleotrophoresis medium of the electrophoresis unit, wherein the compartments are disposed and adapted such that the electrophoresis unit assumes a standing position in the apparatus.

Because the electrophoresis unit is disposed substantially vertically, a sample can, after placing of the electrophoresis unit in the apparatus and conditioning thereof, be arranged in the electrophoresis medium via an upper side, whereafter by starting the electrophoresis via the pairs of electrodes electrophoresis can take place successively in the first dimension and the second dimension.

A particularly simple construction of the apparatus according to the invention is obtained when in preference an electrophoresis tank is sub-divided by two dividing walls into two outer compartments forming one of both pairs and a middle compartment which forms with an electrophoresis liquid container to be placed in the apparatus the other pair of compartments. In this case the electrophoresis unit extends into the middle compartment which can be filled partially or for a greater part with electrophoresis liquid. A division can nevertheless be realized with an electrophoresis liquid container to be placed thereabove. It is however noted that a liquid container can be omitted and instead the middle compartment can be provided with an upper dividing wall through which passes the electrophoresis unit.

For optimum arrangement of the electrophoresis unit in the apparatus according to the invention it is further recommended that in the dividing walls slots are arranged through which the electrophoresis unit makes contact with the outer compartments and more preferably that in the electrophoresis liquid container slots are arranged through which the electrophoresis unit makes contact with the electrophoresis liquid present in the electrophoresis liquid container.

In order to avoid artefacts from electrophoresis it is recommended that the electrophoresis current between the two electrodes substantially passes through only the electrophoresis medium and substantially a good sealing must be present between the compartments during electrophoresis. The liquid sealing can be realized by liquid-repellent substances on the plates and/or slots but preferably in that slots are provided with means for forming a liquid sealing between the slots and the electrophoresis unit extending into the slots. If more than one electrophoresis unit can be mounted in the apparatus according to the invention it is further recommended that the sealing means also seal the slots when no electrophoresis unit is mounted in a slot.

Because the electrophoresis for the first dimension is generally performed a horizontal direction, it is possible that artefacts or may occur under the influence of the force of gravity and/or the form and manner of arranging the sample for electrophoresis. These defects can be avoided by influencing the pattern of the electrical lines of flux in the electrophoresis medium, for instance in that the electrical lines of flux converge in the electrophoresis direction opposite to the direction of the force of gravity. It is therefore recommended that the electrophoresis unit makes contact with its standing sides with the first pair of compartments and with its lying sides with the second pair of compartments, and at least one of the standing sides is provided with an electrically insulating element which interrupts the electrophoretic contact over a part of the side length.

Depending on the form and size of the sample cavity and the width over which the first-dimensional electrophoresis is performed in the horizontal direction, it can be advantageous if in further preference both standing sides are provided with an electrically insulating element. In this case optimum dividing patterns are generally realized if more preferably both electrically insulating elements are of unequal length. In general the most optimal divisions are realized if in further preference the electrophoresis medium is provided on the upper lying side with a sample cavity and/or the longest electrically insulating element is located on the standing side situated at the greatest distance from the sample cavity.

This electrically insulating element preferably has a length such that its top end extends some distance below the underside of the sample cavity (for instance 10–100% of the sample cavity length). The electrically insulating element located on the other side has an equal or smaller length, for instance 100–10%, in general 100–50% of the length of the electrically insulating element located on the other side.

In order to avoid as far as possible diffusion of the sample arranged in the electrophoresis medium and the resulting artefacts, it is further recommended that a sample cavity arranged in the electrophoresis medium has a form narrowing in the direction into the electrophoresis medium. In particular the sample cavity has a narrowed form such that a rearmost mould cavity wall stands substantially perpendicularly of the electrical field to be applied.

Another aspect of the present invention relates to an electrophoresis unit which can be used in the electrophoresis apparatus according to the invention. In particular this electrophoresis unit is characterized by the presence, form and length of one or more electrically insulating elements which can extend along or between the plates.

Mentioned and other features of the electrophoresis apparatus and the electrophoresis unit according to the invention will be further elucidated hereinafter on the basis of a number of non-limitative embodiments given by way of example, wherein reference is made to the annexed drawings.

BRIEF DESCRIPTION OF THE DRAWINGS

In the drawing:

FIGS. 6–9 each show a front view of another electrophoresis unit according to the invention.

DESCRIPTION OF THE PREFERRED EMBODIMENTS

Figure 1:
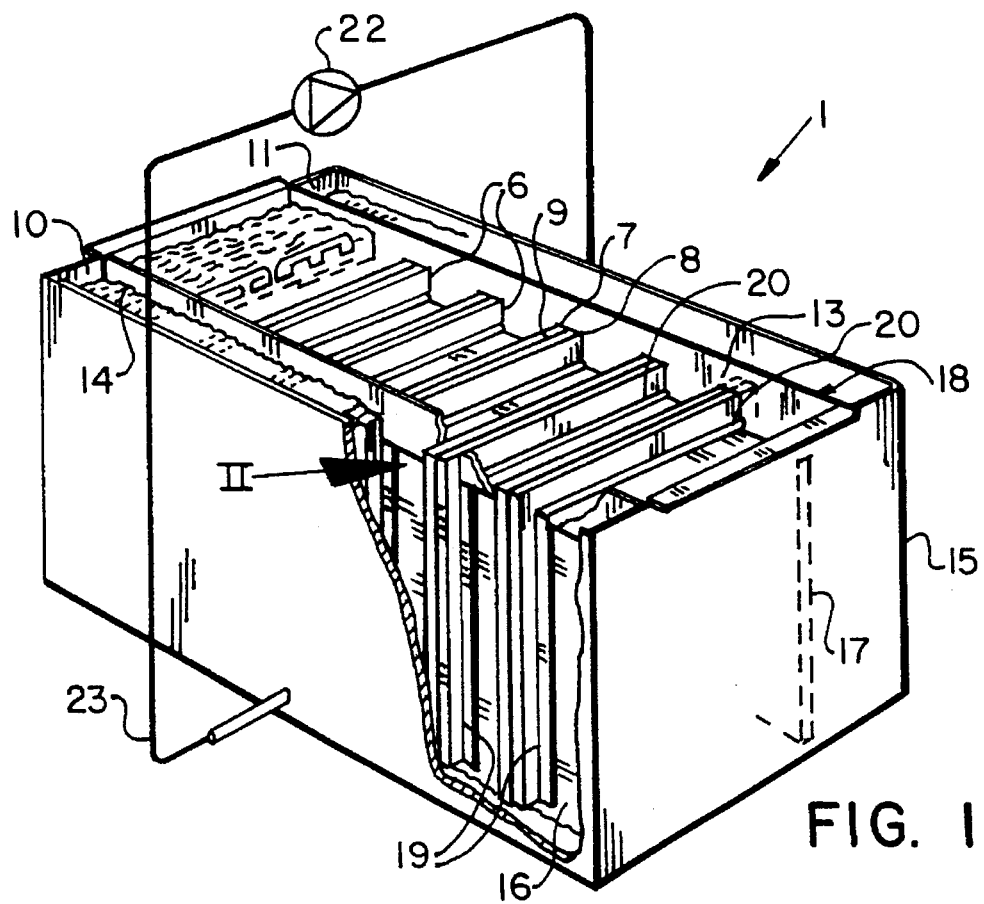
FIGS. 1, 3–5 each show a variant of an electrophoresis apparatus according to the invention.

FIG. 1 shows an apparatus 1 according to the invention for two-dimensional electrophoresis of in this case six electrophoresis units which comprise electrophoresis medium 9 enclosed between two plates, for instance glass plates 7 and 8.

The apparatus 1 comprises a first pair of compartments 10 and 11 and a second pair of compartments 12 and 13. Each compartment 10–13 is provided with an electrode (not shown in this case) and is filled with electrophoresis liquid which, subject to the type of electrophoresis to be performed, can have in both dimensions the same or mutually differing composition.

The apparatus 1 is constructed from an electrophoresis tank 15 which is sub-divided by two dividing walls 16 and 17 into the outer compartments 10 and 11 of the first pair and a middle compartment 12 of the second pair. The other compartment 13 of the second pair is formed by an electrophoresis liquid container 18 which is placed in the electrophoresis tank 15 above the compartment 12.

Figure 2:
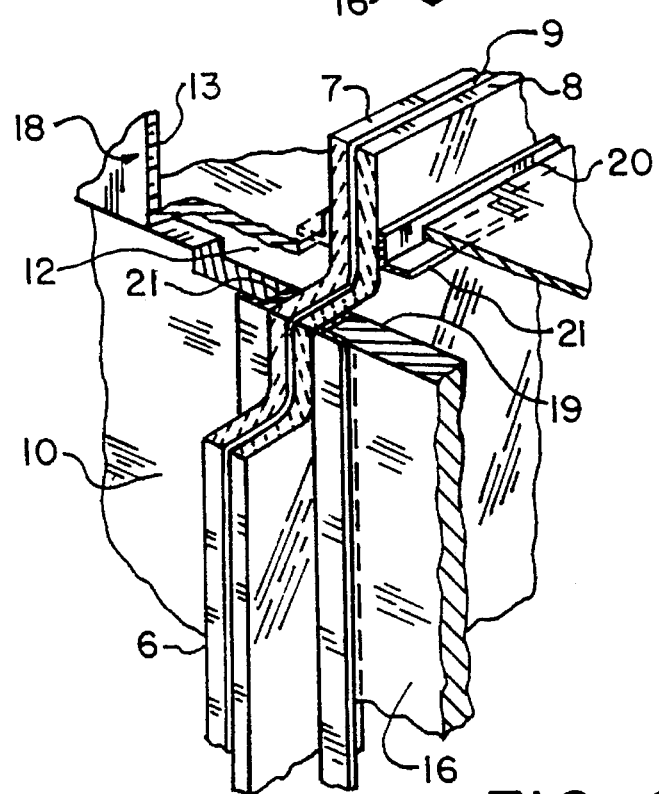
FIG. 2 shows on a larger scale detail II of FIG. 1.

As shown in FIG. 2, the dividing walls 16 and 17 are provided with slots 19 through which the electrophoresis unit 6 protrudes into the outer compartments 10 and 11 and makes contact therein with the present electrophoresis liquid 14.

The electrophoresis container 18 is also provided with slots 20 through which the electrophoresis unit protrudes into the compartment 13.

Slots 19 and 20 are provided with means with which a liquid sealing is realized between the slots 19 and 20 and the electrophoresis unit 6 extending through the slots. These sealing means consist for instance of angled, elastic rubber profiles 21 with a form such that when the electrophoresis unit 6 is removed the slots are closed by the co-acting rubber profiles. Because the electrophoresis container rests on the dividing walls 16 and 17 an adequate liquid sealing is realized between on one side the electrophoresis container 18 and on the other the other compartments 10–12.

The compartments 10 and 11 are mutually connected via a circuit 23 provided with a pump 22 so that the composition of the electrophoresis liquid 14 is substantially the same in both compartments. Temperature differences are moreover avoided as far as possible.

The electrodes (not shown) are connected to a control unit so that the electrophoresis can be performed in both dimensions semi-automatically or automatically after the electrophoresis units 6 have been placed in the apparatus 1. Activation of pump 22 is carried out by the same control unit.

Figure 3:
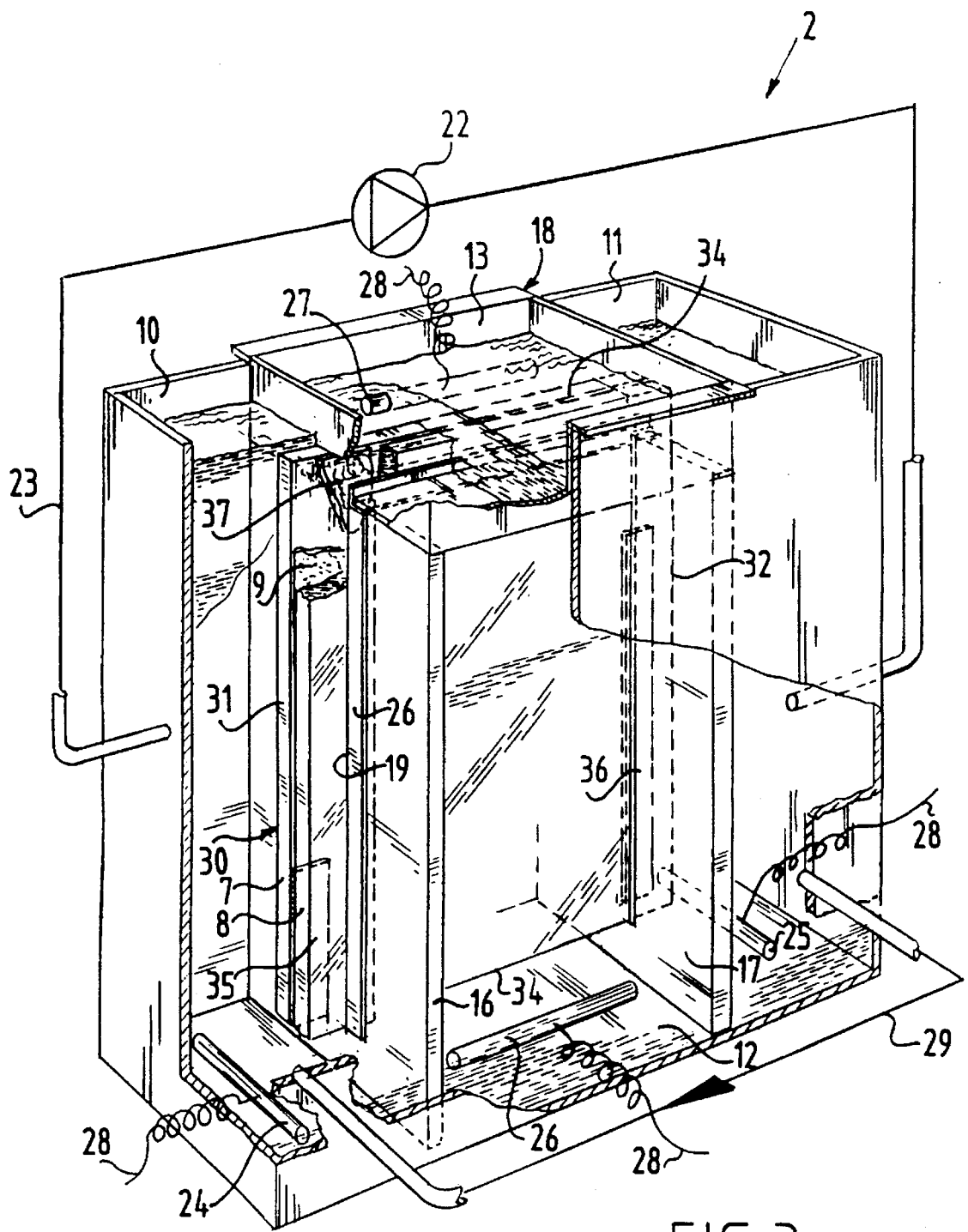

FIG. 3 shows an electrophoresis apparatus 2 according to the invention having substantially the same construction as the apparatus 1 of FIG. 1. Compartments 10 and 11 and the middle compartment 12 are mutually separated by the dividing walls 16 and 17 and compartment 13 is again formed by an electrophoresis container 18. As shown, all compartments are provided with an electrode 24–27 which is connected via an electrical connection 28 to the control unit (not shown). The circuit 23 also comprises as shown a communicating conduit 29.

The electrophoresis unit 30 which is arranged in an apparatus 2 comprises two standing sides which extend into the respective compartments 10, 11. The bottom lying side 34 is situated in the compartment 12 and the upper lying side is situated in the container-like compartment 13.

The electrophoresis unit 30 comprises two electrically insulating elements 35 and 36 which lie between both glass plates 7 and 8. The electrical element 35 interrupts the electrophoretic contact with the electrophoresis medium 9 over only a small part of the side length, but the electrically insulating element 36 interrupts the electrophoretic contact over a considerable part of the side length to some distance below the sample cavity 37 which has a form narrowing in the direction into the electrophoretic medium.

Figure 4:
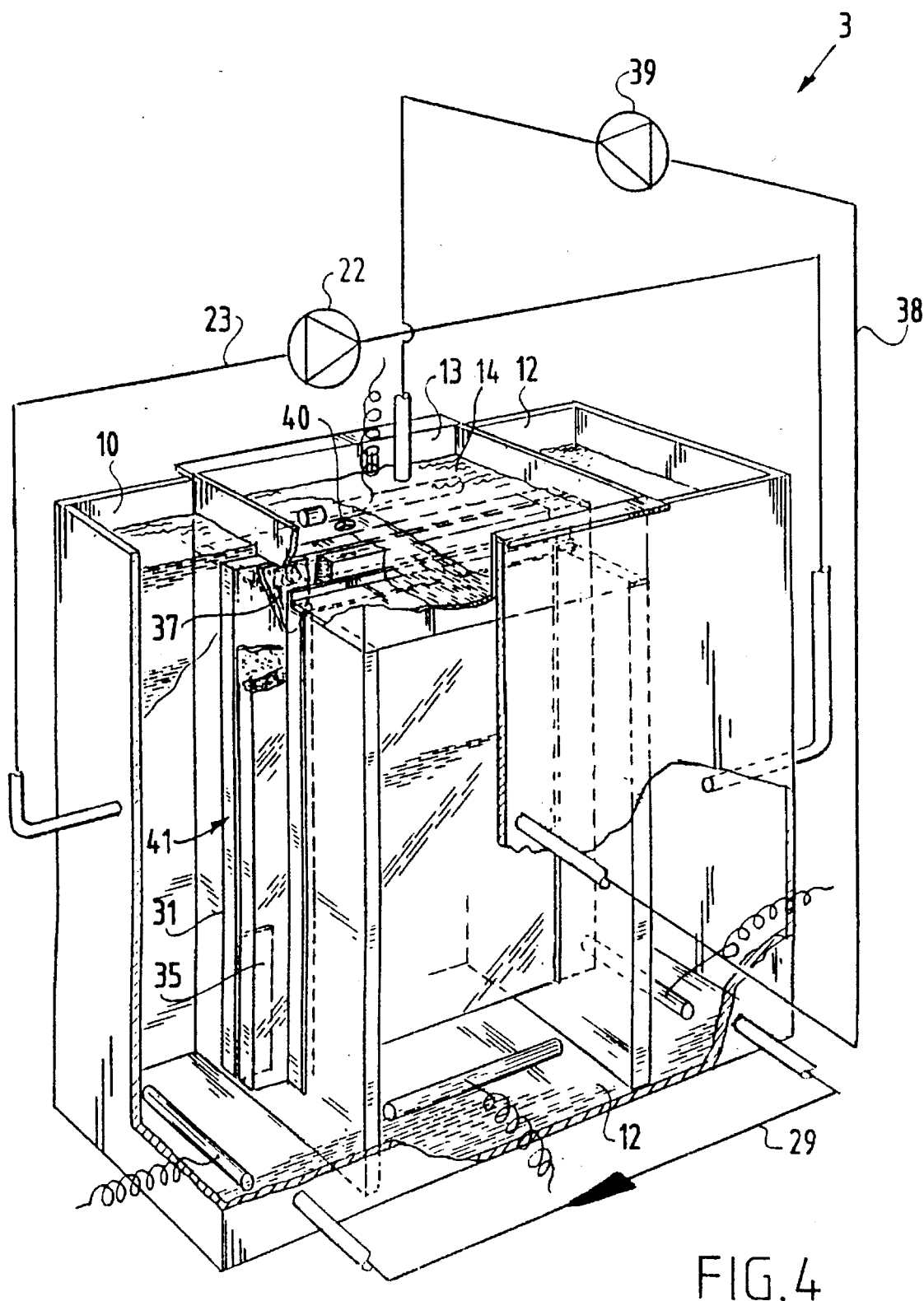

The electrophoresis apparatus 3 of FIG. 4 has substantially the same construction as the apparatus 2 of FIG. 3. In this case however, the compartments 12 and 13 also form a circuit 38 with a pump 39 arranged therein. From the container-like compartment 13 electrophoresis is liquid 14 flow via an opening 40 to compartment 12. Arranged in the apparatus 3 in this case is an electrophoresis unit 41 which is provided only on its side 31 with an electrically insulating element 35.

The pump 39 is in this case also connected to the control unit (not shown).

Figure 5:
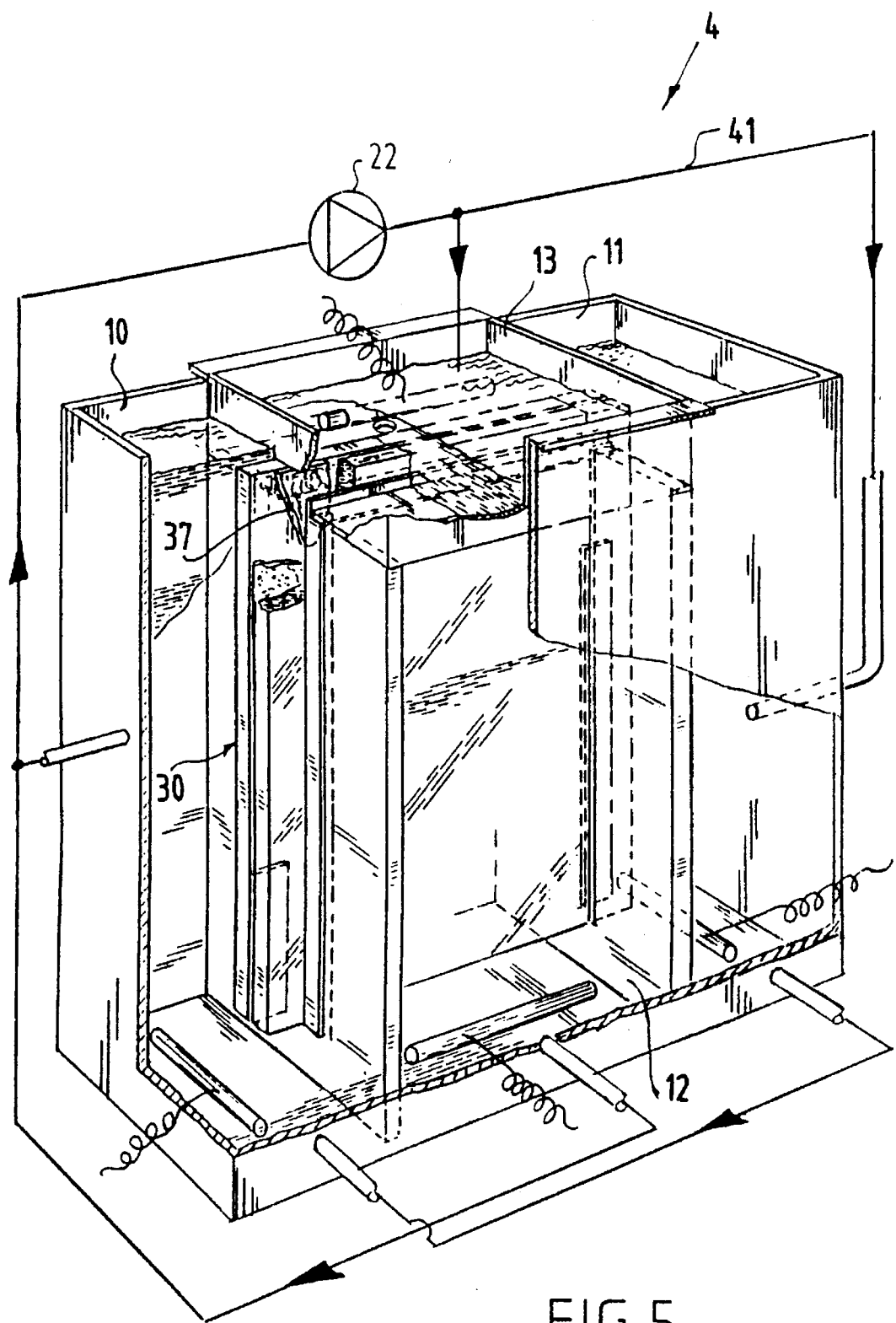

FIG. 5 shows an electrophoresis apparatus 4 according to the invention having substantially the same construction as the apparatus 2 and 3. This apparatus is provided with only one circuit 41 with a pump 22 arranged therein, so that the compartments 10–13 are in mutual contact. By if necessary including closing valves in circuit 41, electrophoresis liquid can be circulated in any desired sense into and out of each of compartments 10–13.

FIG. 6 shows an electrophoresis unit 43 according to the invention with a sample cavity with a narrowing form formed on the top side in the electrophoresis medium, while a cavity wall 44 stands substantially transversely of the electrical field to be applied.

The electrophoresis unit 45 shown in FIG. 7 comprises a very narrow sample cavity 37 on the upper lying side 32. The standing side 33 is moreover provided with an electrically insulating element 46 which extends over a considerable part of the side length to some distance from the lowest point of the sample cavity 37.

FIG. 8 shows an electrophoresis unit 47 according to the invention, wherein the standing sides 31 and 33 are each provided with an electrically insulating element 48 and 49 of mutually equal length which also extend over a considerable part of the side length to some distance below the sample cavity 44.

FIG. 9 shows an electrophoresis unit 50 with a very narrow sample cavity, wherein in this case the standing sides 31 and 33 are each provided with an electrically insulating element 51 and 52 of mutually differing length. The length of electrically insulating element 52 is greater than that of element 51 resulting in a converging of the electrical lines of flux from the sample cavity 37 to the part of the side 33 making electrophoretic contact.

Figure 10:
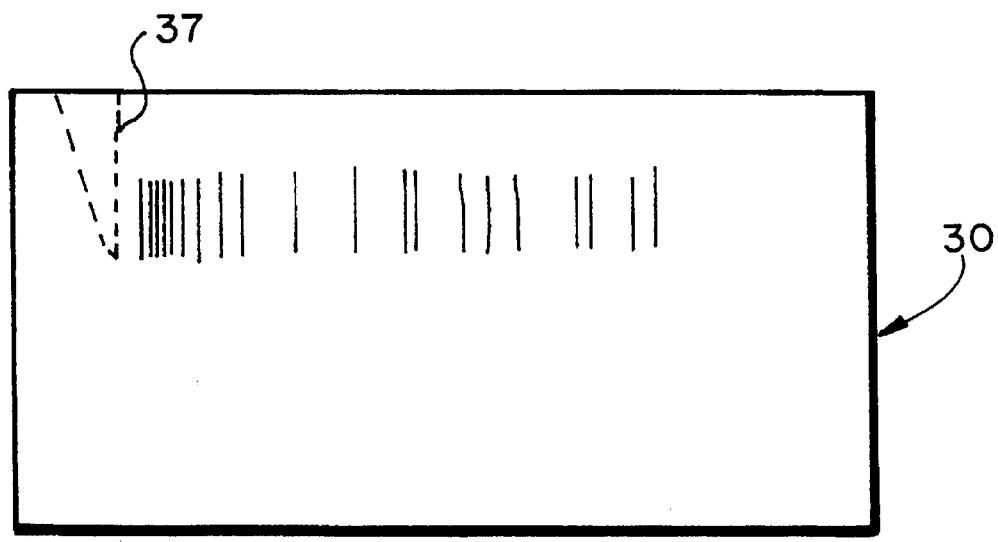
FIGS. 10–12 show electrophoresis patterns obtained with the apparatus according to the invention.
Figure 11:
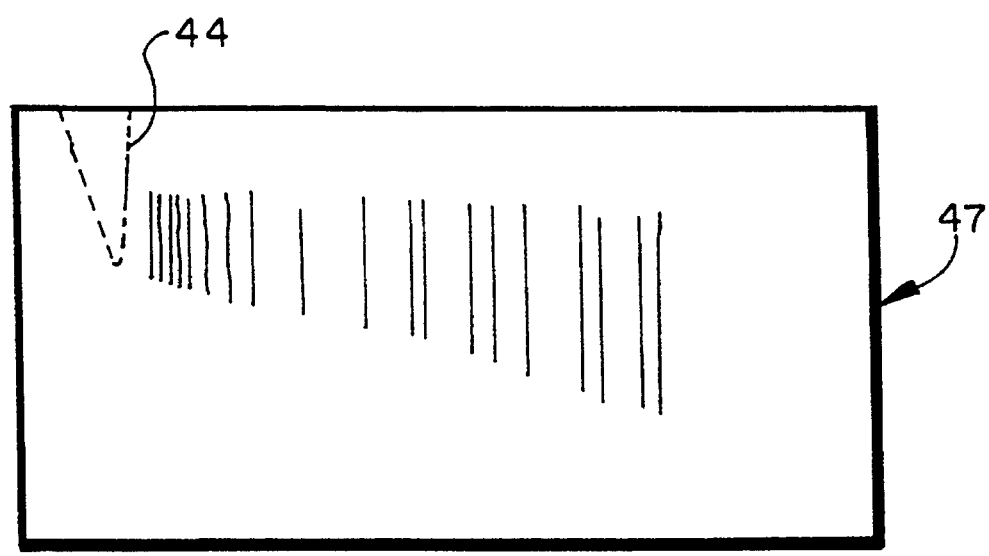

FIGS. 10 and 11 show the effect of the use of electrically insulating elements according to the invention.

FIG. 10 shows the upper portion of the electrophoresis unit 30 and FIG. 11 the upper portion of the electrophoresis unit 47 after a mixture of Marker-DNA fragments obtained after a treatment with restriction enzymes of Faag-Lambda-DNA was placed in the sample cavities 37 respectively 44.

Figure 12:
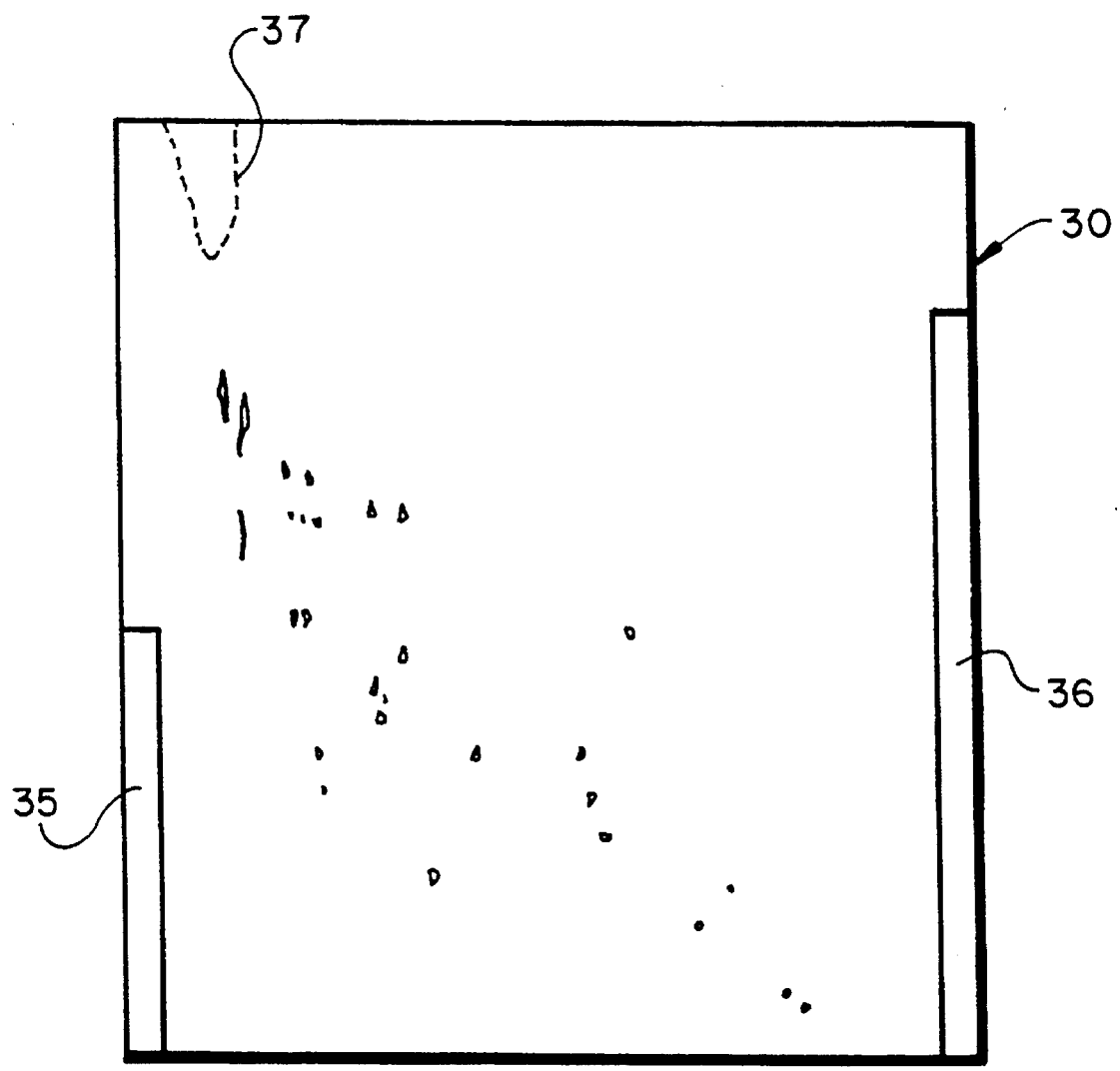

Finally, FIG. 12 shows the electrophoresis unit 30 after electrophoresis has been performed in two dimensions in the apparatus 2 according to FIG. 3.

It is recommended that during the first electrophoresis between the compartments 10 and 11 the middle compartment 12 is filled to below the upper edge of the electrophoresis unit 30. During the second electrophoresis the said compartments are preferably empty and the compartments 12 and 13 filled.

It will be apparent that for the electrophoresis unit according to the invention any type of suitable electrophoresis medium can be used, for example agarose and polyacrylamide and in addition carbon-comprising carriers such as silica and alumina. Furthermore, different types of electrophoresis media can be used in one electrophoresis unit for the two successive electrophoreses performed in different dimension. Finally, it is possible after for instance electrophoresis in one dimension to perform a biochemical reaction on the obtained pattern and only thereafter to carry out electrophoresis in the subsequent direction.

We claim:

1. An apparatus for two-dimensional electrophoresis provided with at least one electrophoresis unit comprising an electrophoresis medium enclosed between two plates, which apparatus comprises a first pair and a second pair of compartments for electrophoresis liquid, herein the compartments are disposed such that the electrophoresis unit assumes a standing position in the apparatus, wherein electrodes are provided in the compartments, wherein the electrophoresis unit has sides and the first pair and second pair of compartments contact the sides of the electrophoresis unit and wherein the electrophorectic contact of the first pair of compartments with the electrophoresis medium between the two plates is transverse to the electrophoretic contact of the second pair of compartments with the electrophoresis medium between the two plates.

2. The apparatus as claimed in claim 1, further including an electrophoresis tank sub-divided by two dividing walls into two outer compartments forming the first pair of compartments and a middle compartment which forms with an electrophoresis liquid container to be placed in the apparatus the second pair of compartments.

3. The apparatus as claimed in claim 2, wherein slots are arranged in the dividing walls through which the electrophoresis unit makes contact with the outer compartments.

4. The apparatus as claimed in claim 3, wherein the slots are provided with means for forming a liquid sealing between the slots and the electrophoresis unit extending into the slots.

5. The apparatus as claimed in claim 4, wherein the electrophoresis unit makes contact with its standing sides with the first pair of compartments and with its lying sides with the second pair of compartments, and at least one of the standing sides is provided with an electrically insulating element which interrupts the electrophoretic contact over a part of the side length.

6. The apparatus as claimed in claim 3, wherein in the electrophoresis liquid container slots are arranged through which the electrophoresis unit makes contact with the electrophoresis liquid present in the electrophoresis liquid container.

7. The apparatus as claimed in claim 3, wherein the electrophoresis unit makes contact with its standing sides with the first pair of compartments and with its lying sides with the second pair of compartments, and at least one of the standing sides is provided with an electrically insulating element which interrupts the electrophoretic contact over a part of the side length.

8. The apparatus as claimed in claim 3, wherein a sample cavity arranged in the electrophoresis medium has a form narrowing in the direction into the electrophoresis medium.

9. The apparatus as claimed in claim 2, wherein slots are arranged in the electrophoresis liquid container through which the electrophoresis unit makes contact with the electrophoresis liquid present in the electrophoresis liquid container.

10. The apparatus as claimed in claim 9, wherein the slots are provided with means for forming a liquid sealing between the slots and the electrophoresis unit extending into the slots.

11. The apparatus as claimed in claim 9, wherein the electrophoresis unit makes contact with its standing sides with the first pair of compartments and with its lying sides with the second pair of compartments, and at least one of the standing sides is provided with an electrically insulating element which interrupts the electrophoretic contact over a part of the side length.

12. The apparatus as claimed in claim 2, wherein the electrophoresis unit makes contact with its standing sides with the first pair of compartments and with its lying sides with the second pair of compartments, and at least one of the standing sides is provided with an electrically insulating element which interrupts the electrophoretic contact over a part of the side length.

13. The apparatus as claimed in claim 2, wherein a sample cavity arranged in the electrophoresis medium has a form narrowing in the direction into the electrophoresis medium.

14. The apparatus as claimed in claim 1, wherein a sample cavity arranged in the electrophoresis medium has a form narrowing in the direction into the electrophoresis medium.

15. An apparatus for two-dimensional electrophoresis provided with at least one electrophoresis unit comprising an electrophoresis medium enclosed between two plates, which apparatus comprises a first pair and a second pair of compartments for electrophoresis liquid, wherein the compartments are disposed such that the electrophoresis unit assumes a standing position in the apparatus, wherein electrodes are provided in the compartments, wherein the electrophoresis unit includes standing sides and lying sides, wherein the first pair and second pair of compartments contact the sides of the electrophoresis unit, wherein the electrophoretic contact of the first pair of compartments with the electrophoresis medium between the two plates is transverse to the electrophoretic contact of the second pair of compartments with the electrophoresis medium between the two plates, wherein the electrophoresis unit makes contact with its standing sides with the first pair of compartments and with its lying sides with the second pair of compartments, and wherein at least one of the standing sides is provided with an electrically insulating element which interrupts the electrophoretic contact over a part of the at least one standing side.

16. The apparatus as claimed in claim 15, wherein both standing sides are provided with an electrically insulating element which interrupts the electrophoretic contact with the electrophoresis medium over a part of each standing side.

17. The apparatus as claimed in claim 16, wherein the electrically insulating elements are of unequal length.

18. The apparatus as claimed in claim 17, wherein the electrophoresis medium is provided on an upper lying side with a sample cavity and a longest electrically insulating element is located on the standing side situated at the greatest distance from the sample cavity.

19. The apparatus as claimed in claim 16, wherein one of the electrically insulating elements is a longest electrically insulating element, the electrophoresis medium is provided on an upper lying side with a sample cavity and the longest electrically insulating element is located on the standing side situated at the greatest distance from the sample cavity.

20. The apparatus as claimed in claim 15, wherein one of the electrically insulating elements is a longest electrically insulating element, the electrophoresis medium is provided on an upper lying side with a sample cavity and the longest electrically insulating element is located on the standing side situated at the greatest distance from the sample cavity to interrupt the electrophoretic contact with the electrophoresis medium over a part of the standing side situated at the greatest distance from the sample cavity.

* * * * *

UNITED STATES PATENT AND TRADEMARK OFFICE
CERTIFICATE OF CORRECTION

PATENT NO. : 5,562,813
DATED : October 8, 1996
INVENTOR(S) : Erik Mullaart, André G. Uitterlinden and Jan Vijg It is certified that error appears in the above-indentified patent and that said Letters Patent is hereby corrected as shown below:

Column 1 Line 40 "numbers or" should read --numbers of--.

Column 2 Line 41 before "a" insert --in--.

Column 2 Line 42 before "may" insert --deformations--.

Column 4 Line 53 after "electrophoresis" delete "is".

Column 4 Line 54 "flow" should read --flows--.

Column 5 Line 50 "dimension." should read --dimensions.--.

Claim 1 Line 59 Column 5 "herein" should read --wherein--.

Claim 1 Line 65 Column 5 electrophorectic" should read --electrophoretic--.

Signed and Sealed this

Seventh Day of January, 1997

Attest:

BRUCE LEHMAN

*Attesting Officer*  *Commissioner of Patents and Trademarks*